United States Patent [19]  [11] 3,949,087
Bacq et al. [45] Apr. 6, 1976

[54] METHOD OF SUPPRESSING SEBORRHEA
[75] Inventors: Zénon Bacq, Liege; Fernand Binon, Strombeek-Bever, both of Belgium
[73] Assignee: Labaz, Paris, France
[22] Filed: Aug. 5, 1974
[21] Appl. No.: 494,523

Related U.S. Application Data
[63] Continuation of Ser. No. 269,036, July 5, 1972, abandoned.

[30] Foreign Application Priority Data
July 6, 1971 France............................ 71.24611

[52] U.S. Cl. ............ 424/319; 424/DIG. 4; 424/70; 424/365
[51] Int. Cl.² .................. A61K 7/06; A61K 31/195
[58] Field of Search............................... 424/319, 70

[56] References Cited
UNITED STATES PATENTS
3,694,547   9/1972   Forsthoff....................... 424/DIG. 4
FOREIGN PATENTS OR APPLICATIONS
1,281,230   12/1961   France............................... 424/316

OTHER PUBLICATIONS

American Perfumer & Cosmetics, 2/1970, Vol. 85, pp. 47 to 51.

Acta–Dermato–Vemereology, 1954, Vol. 54, pp. 272 to 278.

American Perfumer & Cosmetics, 1966, pp. 23 to 24, Vol. 81.

Drug & Cosmetic Industry, 3/1952, Vol. 70, No. 3, pp. 320, 321 and 420–425.

*Primary Examiner*—Dale R. Ore
*Attorney, Agent, or Firm*—Mason, Kolehmainen, Rathburn & Wyss

[57] ABSTRACT

A method of suppressing seborrhea whereby there is applied to the affected area a composition containing as active principle in a nontoxic vehicle $\alpha$,l-carnitine chloride or l-carnitine chloride or a mixture of these two substances.

3 Claims, No Drawings

METHOD OF SUPPRESSING SEBORRHEA

This application is a continuation of our copending application Ser. No. 269,036 filed July 5, 1972, now abandoned, which claims priority based on French application No. 71.24611 filed July 6, 1971.

The present invention relates to compositions for combating seborrhoeic conditions containing as active principle at least one of the substances hereinafter referred to as d,l-carnitine chloride or l-carnitine chloride and corresponding to the formula:

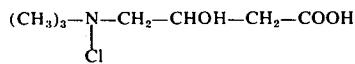

considered under its racemic and laevogyrous forms.

The compositions of the invention are for cosmetic use and have proved to be very valuable in all cases where the condition of the skin can be improved by the suppression or the reduction of seborrhoea.

d,l-Carnitine and l-carnitine chlorides are known substances.

d,l-Carnitine chloride may be obtained by various processes either from natural sources or by synthesis. Carnitine may be extracted, for example, by precipitation as a chloroaurate, Reineckate or mercuric complex from fractions taken from muscle extract, meat extract or whey. The substance may be prepared in various ways, for example, from γ-dimethylamino-β-hydroxybutyronitrile chloromethylate which is hydrolysed, not directly, but through the corresponding ethyl imino-ether or from γ-amino-β-hydroxybutyric acid as described in the preamble to British Pat. No. 912,019.

However, these methods of obtaining d,l-carnitine chloride are not very effective. On the other hand, the process of preparing d,l-carnitine chloride as claimed in the above British Pat. No. 912,019 is much more advantageous. According to this process, which is illustrated by Examples 1a, 1b, 1c and 1d hereunder, γ-dimethyl-amino-β-hydroxybutyronitrile chloromethylate is hydrolysed with from 1 to 2½ times its weight of concentrated aqueous hydrochloric acid, containing not less than 30% by weight of hydrochloric acid and optionally saturated with HCl gas, at a temperature of from 50° to 80°C, preferably 70° to 80°C, the hydrolysis product is cooled to about 0° to 5°C, the ammonium chloride and any other impurities which may be formed are filtered out, and the d,l-carnitine chloride separated out by treating the hydrolysis product with a reagent selected from the group comprising isopropyl alcohol, ethyl alcohol, acetone and concentrated aqueous hydrochloric acid, the solvent is eliminated and the d,l-carnitine chloride washed with isopropyl alcohol or acetone and dried.

d,l-Carnitine chloride as well as l-carnitine chloride may also be prepared by the process claimed in British Pat. No. 1,075,564 from d,l- and l-carnitinamide chloride respectively. According to this process d,l-carnitinamide chloride or l-carnitinamide chloride are treated as follows:

Either:

a. By refluxing in an aqueous solution of oxalic acid for a period ranging from about 1 hour to about 10 hours according to the concentration of oxalic acid, cooling the solution, eliminating the oxalic acid and ammonium oxalate which forms, evaporating the resulting solution under vacuum, taking up the residue so formed in an alcohol and cooling the alcoholic solution to about 0°C so as to crystallise out the carnitine chloride.

Or:

b. By mixing the carnitinamide chloride with an alkyl nitrite and glacial acetic acid, heating the resulting mixture for about 20 hours at about 50°C, cooling the resulting solution to about 10°C which in the case of the racemic amide causes d,l-carnitine chloride crystals to precipitate and, when the starting amide is optically active, adding to the cooled solution a nonpolar precipitation agent which causes the l-carnitine chloride to precipitate in the form of an oil which is crystallized from an alcohol.

Finally, the crystals thus formed are separated out from the cooled solution.

This process is illustrated by Examples 2a, 2b, 2c and 2d hereunder.

The invention therefore includes the processes of preparation of d,l-carnitine and l-carnitine chlorides as substances having anti-sebrrhoeic activity.

The chlorides of d,l-carnitine and l-carnitine are already recognized as possessing biological activity of value to humans and animals. They enable a better employment by the tissues of lipids in cases of metabolic imbalance and, in particular, denutrition syndromes of various origins, hypotropy, senescence and cachexia.

All these activities occur inside the body and necessitate the use of carnitine by internal route. None of them, moreover, suggests that the compositions of the present invention, where carnitine is presented for the first time in a form suitable for external application, could be of considerable value in the field of cosmetology by suppressing or diminishing seborrhoea to an appreciable degree.

There exists at present a large number of substances which are used to combat seborrhoea. It may, however, be said that they are all either only slightly active or are accompanied by undesirable side-effects.

Certain of these substances are based on oestrogens and appear to be effective against seborrhoea. However, they exert biological effects even in therapeutic doses which in men are feminizing and in women often disturb the menstrual cycle and cause gastric irritation. Their use also involves a not inconsiderable risk of thrombo-embolic complications.

Other substances are based on the antiandrogens. However, this class, although apparently fairly effective against seborrhoea, has not been studied to a sufficient degree, so that the long-term effects are completely unknown. It is known, for example, that 17 α-methyl-β-nortestosterone reduces seborrhoea but exerts a feminizing effect in male subjects.

Yet other substances are characterized by the power to reduce the lipid-level of the blood but their use has not given the results which had been hoped for. Some are clearly inactive while others, when used topically, are irritant as well as fairly inactive.

The very fact that there exists a large number of anti-seborrhoeic products is indicative of a general lack of efficacy as one or a few really effective agents would have sufficed to eliminate all the other less active substances.

The compositions of the invention do not possess the disadvantages enumerated above. In the first place it has been observed that the compositions of the invention are effective in suppressing seborrhoea while, at the same time, the fact that they are based upon carnitine precludes the undesirable side-effects characteristic of the substances cited above. Furthermore, the anti-seborrhoeic effects which have been observed with the compositions of the invention are such that it would not be unreasonable to suggest that they may well exert a regulating effect upon the sebaceous glands in addition to their action on the sebum itself.

With regard to this latter point, it has been reported in the literature — see, for example, Chemistry and Industry, May 22, 1965, page 874 and Arch. Bioch. Bioph., 1967, 119, 583 — that d,l-carnitine and l-carnitine play an important part in the oxidation of free fatty acids. Since the free fatty acid content of human sebum is in the region of 30%, it could be reasoned that the anti-seborrhoeic action of carnitine is exerted through its oxidizing effect on the free fatty acids. However, this hypothesis does not provide a fully satisfactory explanation for the action of carnitine on seborrhoea.

In the first instance, the free fatty acid content of human sebum is, as stated above, about 30%. The remaining 70% is made up mainly of squalene (11%), esters of aliphatic alcohols and sterols (26%) and triglycerides (20%) against which carnitine exerts no known effect. Thus it would appear reasonable to presume that the anti-seborrhoeic action of carnitine is not confined to its oxidizing effect upon the free fatty acids of sebum but involves other phenomena of which the mechanism is as yet unexplained.

A similar conclusion is reached when the problem is considered from the point of view of one of the more unpleasant consequences to which seborrhoea can lead, namely acne. It has long been held that seborrhoea plays an important role in the generation of acne. From this it could be reasoned that the free fatty acids, as a major constituent of sebum, make a not inconsiderable contribution to the formation of acne. However, it has been observed that the free fatty acid content of sebum does not vary whether acne be present or not (J. Pharmac. Sci., 1969, 58, (5), 582–85). On the other hand, it has been found that when acne is present the sebum is poor in triglycerides and rich in esters of aliphatic alcohols (Br J. Derm. 1970, 82, 243). Since the anti-seborrhoeic effect of carnitine has been observed to lead to marked improvement of acneic states, it may be reasonably supposed that the action of carnitine is not confined to the free fatty acids but, as stated above, implies other mechanisms which owe their surprising nature to the fact that they cannot as yet be explained and were, prior to the present invention, completely unexpected.

Another object of the invention is therefore a method of suppressing or diminishing seborrhoea by the external application to the skin of a composition containing as active principle at least one of the substances defined in the above general formula.

By their anti-seborrhoeic action, the compositions of the invention serve not only to combat the undesirable and even disfiguring effects of seborrhoea but they also contribute to the relief of complications resulting from seborrhoea such as acne, eczema, and exzematides when these affections are in fact of seborrhoeic origin.

The compositions of the invention may be presented in any form suitable for external application such as, for example, a lotion, cream or ointment. In each case, the d,l-carnitine or l-carnitine chloride will be associated with the appropriate excipients in accordance with the procedures usually employed for the preparation of such formulations for external use. Suitable excipients may include, for example, distilled water, ethyl alcohol, tetrasodium salt of ethylenediaminetetraacetic acid, benzalkonium chloride, gelot 64 (a mixture of stearic esters of glycerol and polyoxyethyleneglycol), glycol monostearate, cetylic alcohol, isopropyl palmitate, spermaceti, polyoxyethylene sorbitan monostearate, colloidal silica, polyethylene glycol 400, propylene glycol, methyl p-oxybenzoate and propyl p-oxybenzoate together with any basic reagent such as sodium hydroxide and triethanolamine or acid intended to give the composition, if required, a suitable pH value which will preferably be between 4.5 and 5.5.

The invention consequently also includes the process of preparing compositions for external use, having anti-seborrhoeic activity and containing at least one of the substances covered by the above general formula.

By reason of the considerable differences which exist between the composition of the sebum of laboratory animals and that of human sebum, the compositions of the invention were studied on humans.

These trials covered a total of 94 cases presenting exaggerated seborrhoea such as seborrhoeic alopecia, corona seborrhoeica, seborrhoea of the scalp and seborrhoea of the face as well as affections deriving directly from seborrhoea such as acne vulgaris, seborroeic eczema of the face and seborrhoeic eczematides of the face.

In the first series of trials covering 36 cases the following results were obtained.

| | Remission | Improvements Marked | Average | Slight | No Result |
|---|---|---|---|---|---|
| Seborrhoea of the scalp | 2 | 1 | — | — | 1 |
| Seborrhoea of the face | 2 | 1 | — | — | 1 |
| Seborrhoeic alopecia | 8 | — | 1 | — | 1 |
| Acne vulgaris | 7 | 3 | 1 | 1 | — |
| Seborrhoeic eczema of the face | 1 | — | — | — | — |
| Seborrhoeic eczematides of the face | 1 | — | — | — | 1 |

The three remaining cases presented simultaneously seborrhoea of the face, seborrhoea of the scalp and corona seborrhoeica.

These trials were carried out with d,l-carnitine chloride in the form of an aqueous solution and a cream, each form containing 10% of active principle. Each case was treated with two applications of the lotion during the day and one application of the cream in the evening. The trials lasted some 10 days.

The second series of trials covering 58 cases was carried out in accordance with the "double-blind" technique which means that the effect of the active composition was compared to that of a placebo and the doctor who had to examine the results did not know which were due to the active composition and which to the placebo. In this way, the maximum degree of objectivity in the evaluation of the results was ensured.

Initial analysis of the overall results shows that 30 cases were treated with carnitine and 28 with the placebo. The effects obtained are given in the following Table:

|  | marked improvement | Slightly favourable or doubtful result | Failure | Total |
| --- | --- | --- | --- | --- |
| Carnitine | 21 | 1 | 8 | 30 |
| Placebo | 9 | 7 | 12 | 28 |
| Total | 30 | 8 | 20 | 58 |

In the case of seborrhoeic alopecia with which 15 subjects were affected and in that of an infected condition resulting from exaggerated seborrhoea namely acne vulgaris with which 38 subjects were affected the following results were recorded:

Seborrhoeic Alopecia

|  | marked improvement | Slightly favourable or doubtful result | Failure | Total |
| --- | --- | --- | --- | --- |
| Carnitine | 5 | 0 | 1 | 6 |
| Placebo | 4 | 2 | 3 | 9 |
| Total | 9 | 2 | 4 | 15 |

Acne vulgaris

|  | marked improvement | Slightly favourable or doubtful result | Failure | Total |
| --- | --- | --- | --- | --- |
| Carnitine | 15 | 1 | 5 | 21 |
| Placebo | 5 | 3 | 9 | 17 |
| Total | 20 | 4 | 14 | 38 |

This second series of trials was carried out with an aqueous solution of d,l-carnitine chloride containing 10% of active principle. Each case was treated with two applications during the day. The trials lasted about 3 weeks.

No toxic effects or signs of intolerance were observed throughout these trials.

The Examples given hereunder provide a non-limitative illustration of the processes which may be used to prepare the forms of carnitine employed in the compositions for external use of the invention together with various formulations.

EXAMPLE 1

Processes for the preparation of d,l-carnitine chloride from γ-dimethylamino-β-hydroxybutyronitrile chloromethylate a. Proportion of HCl to Chloromethylate : 1 to 1 by weight 2 kg of γ-dimethylamino-β-hydroxybutyronitrile chloromethylate were dissolved in 2 liters of concentrated aqueous hydrochloric acid (38% of HCl by weight). The solution was heated, while stirring, at 75°C for 3 hours at atmospheric pressure in an apparatus fitted with a vertical condenser and stirrer. At the end of this period the hydrochloric solution was cooled and, while still being cooled, was saturated with HCl gas. The solution saturated with HCl was kept at a temperature of about 5°C for about 10 hours by means of a cooling mixture. The $NH_4Cl$ and the non-acid impurities which crystallized under these conditions were removed by filtration when cold. The filtrate was purified, when cold, by means of activated charcoal, after being diluted with a liter of water.

The activated charcoal was filtered out and the hydrochloric solution of carnitine chloride was evaporated under vacuum at a temperature not exceeding 60°C in the evaporation apparatus.

When a degree of evaporation was obtained sufficient to produce crystallization, the operation of evaporation was continued as long as it was reasonably possible to stir the crystals obtained. The crystalline magma was then cooled and suspended in 1600 ml of isopropyl alcohol, in which care was taken to disintegrate the agglomerated masses of crystals. The mixture was filtered and the isopropyl alcohol with which the crystals were impregnated was completely expressed.

The crystals obtained were treated when cold for 4 hours with ordinary ethyl alcohol (94%) in the proportion of 0.7 cc of ethyl alcohol per gram of carnitine chloride. Care had to be taken to ensure that all the crystals were impregnated with alcohol and that all agglomerated masses were completely disintegrated. The mixture was allowed to stand for 4 hours, after which it was filtered until the alcoholic solution was expressed to the maximum. The remaining crystals were washed on the filter with acetone and dried.

Yield : 1600 g.

M.P. 196°C (Decomposition).

b. Proportion of HCl to Chloromethylate : 1 to 1 by weight 2 kg of γ-dimethylamino-β-hydroxybutyronitrile chloromethylate were dissolved in 2 liters of concentrated hydrochloric acid. The hydrolysis reaction was conducted as described in Example 1a except that the concentrated aqueous HCl medium was not saturated with HCl gas. After evaporation of the reaction mixture under vacuum at a temperature not exceeding 60°C the remaining crystals were suspended in about 1600 ml of isopropyl alcohol and the mixture filtered.

The resultant crystals were then almost completely dissolved, when cold, in concentrated HCl (38%) in the proportion of 60 ml of concentrated HCl to 75 g of crude carnitine chloride. Care had to be taken to disintegrate any agglomerated mass of crystals. The solution was stirred slowly for 2 hours, after which it was allowed to stand overnight at 5°C. The non-acid impurities and $NH_4Cl$ which crystallized under these conditions were then filtered out when cold. The remaining solution was evaporated under vacuum at a temperature not exceeding 60°C and the resultant crystals treated with alcohol, washed with acetone and dried as already described in Example 1a.

Yield : 1300 g.

M.P. 196°C (Decomposition).

c. Proportion of HCl to Chloromethylate : 2 to 1 by weight

In accordance with a hydrolysis ratio of 2 liters of HCl/1 kg of chloromethylate the following were placed in a 100 liter enamelled Grignard reaction kettle:

30.0 kg of γ-dimethylamino-β-hydroxybutyronitrile chloromethylate 60.0 liters of 38% concentrated HCl ($D = 1.19$, i.e., 71.4 kg).

To start the reaction the solution was slowly heated, care being taken not to exceed 75°C. The heated solution was then maintained at 75°C for 6 hours, the HCl gas given off being retained in water absorbers (volume of the reaction mass = 85 liters).

The solution was then cooled to about 0°C, by circulating brine, and the $NH_4Cl$ crystals filtered by centrifuge or over a Nutsche filter (volume of the filtrate c. 70 liters). The filtrate was purified, if markedly coloured, with active charcoal, after which it was poured, while being gently stirred, into an acid-resistant vat containing:

180 liters (141.5 kg) of cold isopropyl alcohol (volume of the mixture = c. 250 liters).

The suspension was cooled to about 10°–20°C.

After the precipitation was completed, the precipitate was filtered out over a Nutsche filter and washed first in isopropyl alcohol and then in acetone and dried at 70° to 75°C.

Weight when dry : c. 21.6 kg i.e. 65% of theory.
M.P. 196°C (Decomposition).

d. Proportion of HCl to Chloromethylate : 1.6 to 1 by weight

In accordance with a hydrolysis ratio of 1.6 liters of HCl/1 kg of γ-dimethylamino-β-hydroxybutyronitrile chloromethylate, 50 kg of chloromethylate were hydrolysed for 3 hours at 75°C in 80 liters of concentrated HCl (38%) to give a hydrochloric solution which, after cooling to 0° to 5°C. was centrifuged to eliminate the $NH_4Cl$ and any other impurities which may have formed. The filtrate, if markedly coloured, was treated with active charcoal, filtered and then poured into cold acetone, the suspension so formed being cooled to about 20°C. The figures expressing the yield as regards the product obtained after cooling, centrifuging, and drying at 70° to 80°C, as well as the degree of purity of the product vary according to the quantity of acetone employed. These figures are given below:

| Liters of acetone to 1 kg of chloromethylate | Weight of dry end-product | % of d,l-carnitine chloride | % of olefins expres. in terms of crotonic betaine | $NH_4Cl$ | Volatile matter | Gross Yield |
|---|---|---|---|---|---|---|
| | Kg | % | % | | % | % |
| 40 | 23.4 | 95.1 | 1.4 | 2.0 | 0.5 | 84.5 |
| 20 | 22.7 | 95.7 | 1.2 | 2.3 | 0.4 | 82.1 |
| 10 | 21.8 | 95.9 | 1.0 | 1.8 | 0.6 | 78.9 |
| 8 | 21.7 | 96.4 | 1.2 | 1.7 | 0.4 | 78.5 |
| 6 | 20.9 | 96.6 | 1.1 | 1.6 | 0.5 | 75.6 |
| 4 | 19.0 | 96.9 | 1.1 | 1.7 | 0.3 | 68.75 |

EXAMPLE 2

Processes for the preparation of d,l-carnitine from d,l-carnitinamide chloride a. By means of oxalic acid 3.93 g (0.02 mol) of d,l-carnitinamide chloride were dissolved in 24 ml of water in the presence of 8.6 g (0.068 mol) of crystallised oxalic acid. The resulting solution was heated under reflux for 6 hours. After cooling to about 0°C for at least 6 hours, the greater part of the oxalic acid and the ammonium oxalate was filtered off and the precipitate was washed twice with 24 ml of iced water. The filtrate and the washings were mixed together and concentrated under vacuum until completely dry. To the oily residue were added 40 ml of isopropanol. After crystallization at room-temperature, the mixture was maintained at a temperature of −5°C to 0°C for at least 5 hours in order to ensure complete precipitation. The crystals of d,l-carnitine chloride were then filtered off, M.P. 196°C (Decomposition).

To eliminate any traces of d,l-carnitine oxalate which may be present, the product obtained may be recrystallized from acetic acid, in the proportion of 1 g of d,l-carnitine chloride to 1.3 ml of acetic acid, and in the presence of a slight quantity of hydrochloric acid gas.

Yield : 89.7%.

b. By means of an alkyl nitrite

A mixture of 1.97 g (0.01 mol) of d,l-carnitinamide chloride, 5.05 g (0.049 mol) of n-butyl nitrite, 1.65 ml (0.01 mol) of a solution of hydrogen chloride in ether and 20 ml of acetic acid was heated to about 50°C over a period of 22 hours while stirring. After the solution was cooled to about 10°C the chloride of d,l-carnitine precipitated in the form of crystals which were separated from the reaction medium by filtration.

M.P. 196°C (Decomposition).
Yield : 80.5%.

Processes for the preparation of l-carnitine chloride from l-carnitinamide chloride c. By means of oxalic acid 11.7 g (0.596 mol) of l-carnitinamide chloride were dissolved in a mixture of 24 ml of water and 25.5 g (0.2 mol) of crystallized oxalic acid. The solution was heated under reflux for 6 hours, after which it was cooled to about 0°C for at least 6 hours. The oxalic acid and ammonium oxalate which crystallized were filtered off and then washed twice with 15 ml of iced water. The filtrate was concentrated under reduced pressure and the oily residue dissolved in 117 ml of isopropanol. After filtration to remove any small quantities of insoluble matter which may be present, the solution was placed in a refrigerator at a temperature of about 0°C.

After at least 5 hours in the refrigerator, the crystals of l-carnitine chloride which formed were filtered out, washed with ether and dried under reduced pressure at a temperature not exceeding 50°C.

M.P. 142°C.
Yield : 80%.

d. By means of an alkyl nitrite

A mixture of 1.97 g (0.01 mol) of l-carnitinamide chloride, 5.05 g (0.049 mol) of n-butyl nitrite, 1.65 ml (0.01 mol) of a solution of hydrogen chloride in ether and 20 ml of glacial acetic acid was heated for 22 hours at 50°C, while stirring. After the solution was cooled to about 10°C the l-carnitine chloride which formed was precipitated by adding ether. The supernatant solution was decanted and the oily l-carnitine chloride was redissolved in isopropanol. The solution was filtered and the filtrate cooled to between −5°C and 0°C for several hours. The crude l-carnitine chloride which formed was filtered out.

M.P. 135°–136°C.

After recrystallization from methanol and acetone the product melted at 136°–139°C.

Yield : 82%.

EXAMPLE 3

Aqueous solutions of d,l-carnitine chloride and l-carnitine chloride corresponding to the following formulations were prepared in accordance with known procedures:

| | | |
|---|---|---|
| a) | d,l-Carnitine chloride | 10 g |
| | Sodium hydroxide | q.s. for pH=5 |
| | Distilled water | q.s. for 100 ml |
| b) | l-Carnitine chloride | 5 g |
| | Sodium hydroxide | q.s. for pH=5 |
| | Distilled water | q.s. for 100 ml |

EXAMPLE 4

A cream corresponding to the following formulation was prepared in accordance with known procedures:

| | |
|---|---|
| d,l-Carnitine chloride | 10.00 g |
| Triethanolamine | 7.60 g |
| Glycerol monostearate | 9.15 g |
| Cetylic alcohol | 2.15 g |
| Isopropyl palmitate | 2.15 g |
| Spermaceti | 5.40 g |
| Polyoxyethylene sorbitan monostearate | 3.25 g |
| Colloidal silica | 1.00 g |
| Polyethylene glycol 400 | 10.00 g |
| Methyl p-oxybenzoate | 0.20 g |
| Propyl p-oxybenzoate | 0.02 g |
| Distilled water | q.s. for 100 g |

EXAMPLE 5

An ointment corresponding to the following formulation was prepared in accordance with known procedures:

| | |
|---|---|
| d,l-Carnitine chloride | 10.00 g |
| Triethanolamine | 7.60 g |
| Gelot 64 | 10.00 g |
| Cetylic alcohol | 1.00 g |
| Isopropyl palmitate | 2.50 g |
| Spermaceti | 2.50 g |
| Colloidal silica | 1.00 g |
| Propylene glycol | 10.00 g |
| Methyl p-oxybenzoate | 0.20 g |
| Propyl p-oxybenzoate | 0.02 g |
| Distilled water | q.s. for 100 g |

The minimum quantities of active principle required per square centimeter of skin for one application are:

| | |
|---|---|
| For d,l-carnitine chloride: | 0.1 mg |
| For l-carnitine chloride: | 0.05 mg |

The practical ranges of active substance per square centimeter of skin are:

| | |
|---|---|
| For d,l-carnitine chloride: | 0.1 mg to 0.8 mg |
| with a preferred range of | 0.4 mg to 0.6 mg |
| For l-carnitine chloride: | 0.05 mg to 0.4 mg |
| with a preferred range of | 0.2 mg to 0.3 mg |

In the case of the compositions, the percentage ranges of active principle are the same for cream, ointment and lotion and are:

| | |
|---|---|
| For d,l-carnitine chloride: | 5% to 20% |
| with a preferred range of | 7% to 14% |
| For l-carnitine chloride: | 2.5% to 10% |
| with a preferred range of | 3.5% to 7% |

We claim:

1. Method of suppressing seborrhoea whereby there is applied to the affected area a composition containing as active principle d,l-carnitine chloride or l-carnitine chloride or a mixture of these two substances, the said active principle corresponding to the formula:

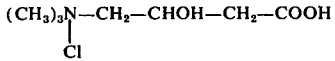

the amount of d,l-carnitine chloride applied being 0.1 mg. to 0.8 mg. per square centimeter and the amount of l-carnitine chloride applied being 0.05 mg. to 0.4 mg. per square centimeter.

2. Method of suppressing seborrhoea according to claim 1 wherein the active principle is d,l-carnitine chloride.

3. Method of suppressing seborrhoea according to claim 1 wherein the active principle is l-carnitine chloride.

* * * * *